US00PP20911P2

(12) United States Plant Patent
Veeder

(10) Patent No.: US PP20,911 P2
(45) Date of Patent: Mar. 30, 2010

(54) ***ECHINACEA* PLANT NAMED 'GREEN QUEEN'**

(50) Latin Name: *Echinacea purpurea*
Varietal Denomination: Green Queen

(76) Inventor: Mark Veeder, 568 Broadway #507, New York, NY (US) 10012

( * ) Notice: Subject to any disclaimer, the term of this patent is extended or adjusted under 35 U.S.C. 154(b) by 0 days.

(21) Appl. No.: 12/291,789

(22) Filed: Nov. 12, 2008

(51) Int. Cl.
*A01H 5/00* (2006.01)

(52) U.S. Cl. ..... Plt./428

(58) Field of Classification Search ..... Plt./428
See application file for complete search history.

*Primary Examiner*—Annette H Para

(57) ABSTRACT

A new and distinct *Echinacea purpurea* cultivar named 'Green Queen' is disclosed, characterized by chartreuse/green flowers, with slight pink blush on the lower ray florets, strong peduncles, and producing many flowers per plant. The new variety is an *Echinacea*, suitable for outdoor and container gardens as well as cut flower production.

1 Drawing Sheet

Figure 1:
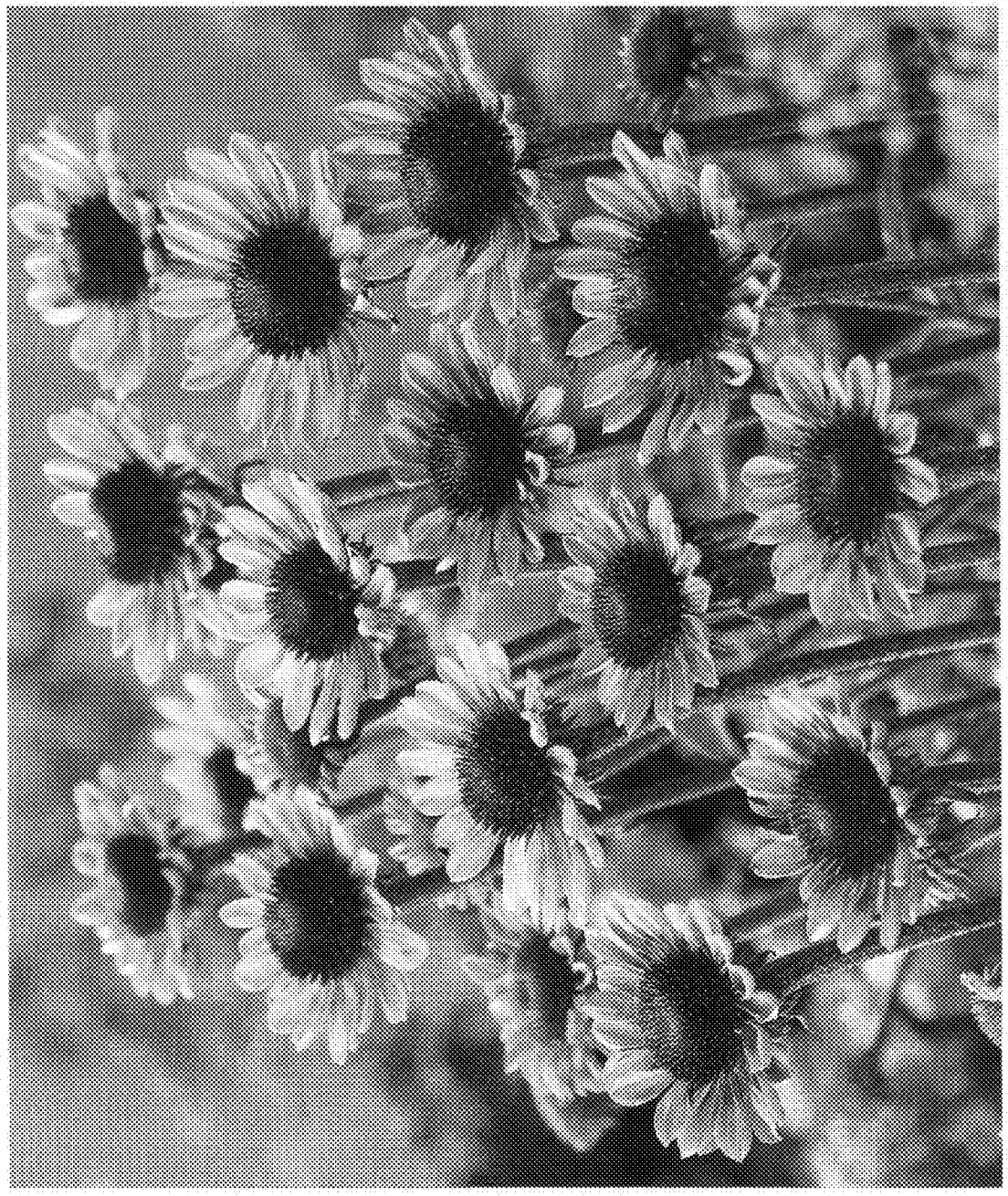

Latin name of the genus and species: *Echinacea purpurea*
Variety denomination: 'GREEN QUEEN'.

BACKGROUND OF THE INVENTION

The new variety was discovered, by the inventor, as a naturally occurring whole plant mutation in a grouping of the parent variety, *Echinacea purpurea* 'Green Envy,' formerly the subject of a U.S. Plant patent application, Ser. No. 11/513,465. It was discovered by the inventor in the summer of 2005.

Asexual reproduction of the new cultivar 'Green Queen' by tissue culture using standard micropropagation techniques with terminal shoots, was first performed in a commercial laboratory in Oregon, beginning in the Spring of 2006 and has shown that the unique features of this cultivar are stable and reproduced true to type in successive generations.

SUMMARY OF THE INVENTION

The cultivar 'Green Queen' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Green Queen' These characteristics in combination distinguish 'Green Queen' as a new and distinct *Echinacea* cultivar:

1. The new variety has a clear green/chartreuse flower.
2. The new variety produces more flowers per plant than similar Echinaceas.
3. The new variety produces a very strong, straight peduncle, suitable cut flower purposes.
4. The plant habit of the new variety is distinctively upright.

PARENTAL COMPARISON

Plants of the new cultivar 'Green Queen' are similar to plants of the parent variety, *Echinacea purpurea* 'Green Envy' in most horticultural characteristics; however, 'Green Queen' produces more flowers per plant than the parent variety. Additionally, 'Green Queen' produces a significantly more stable flower color. Whereas 'Green Envy' has shown to produce almost completely pink flowers out of tissue culture, 'Green Queen' is consistently chartreuse/green, with slight pink coloration near the base of ray florets.

COMMERCIAL COMPARISON

Plants of the new cultivar 'Green Queen' are most similar to plants of the commercial variety, *Echinacea purpurea* 'Green Jewel' U.S. Plant Pat. No. 18,678 in most horticultural characteristics; however, 'Green Queen' produces more flowers per plant than 'Green Jewel.' Additionally, 'Green Queen' is a significantly smaller and more compact plant, approximately half the height and width of 'Green Jewel.'

BRIEF DESCRIPTION OF THE PHOTOGRAPH

The accompanying photograph in FIG. 1 illustrates in full color a typical flowers, peduncles and leaves of 'Green Queen' grown outdoors in the New York state. The plant shown is approximately 7 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Green Queen' plants grown outdoors in New York State from Spring 2008 through Fall 2008. The growing temperature ranged from 10° C. to 16° C. at night to 21° C. to 29° C. during the day. Measurements and numerical values represent averages of typical flowering types.

Botanical classification: *Echinacea purpurea* cultivar 'GREEN QUEEN.'

PROPAGATION

Time to rooting: 40 days at approximately 21° C.

Root description: Fine, well-branched, fibrous, becoming slightly woody with age.

PLANT

Growth habit: Hardy, upright, herbaceous perennial.
Height: Approximately 50 cm.
Blooming period: Naturally blooming Summer to early Fall. Approximately July through August.
Plant spread: Approximately 25 cm.
Growth rate: Moderate.
Branching characteristics: Basal branching, moderately free branching.
Length of lateral branches: Approximately 17.5 cm.
Diameter of lateral branches: Approximately 0.5 cm.
Quantity of lateral branches: Approximately 4.
Texture of lateral branches: Sparsely hirsute.
*Hair color.*—Near RHS Green 138D.
Color of lateral branches: Near RHS Green 138A
Aspect: Approximately 20° angle from base of plant.
Internode length: Approximately 8 cm.
Number of leaves per lateral branch: Approximately 18.
Age of plant described: Approximately 7 months from a rooted cutting.

FOLIAGE

Leaf:
*Arrangement.*—Alternate, simple.
*Average length.*—Smallest apical leaves, approximately 4.2 cm. Largest basal leaves, approximately 12.5 cm.
*Average width.*—Smallest apical leaves approximately 3.2 cm. Largest basal leaves, approximately 8.5 cm.
*Shape of blade.*—Lanceolate.
*Apex.*—Acute.
*Base.*—Attenuate.
*Attachment.*—Apical leaves are sessile. Lower leaves with petioles.
*Margin.*—Serrate.
*Texture of top surface.*—Moderately scabrous.
*Texture of bottom surface.*—Highly scabrous.
*Leaf internode length.*—Approximately 0.9 cm.
*Color.—Young foliage upper side.*—Near RHS Green 138B. Young foliage under side: Near RHS Green 137C. Mature foliage upper side: Near RHS Green 138A. Mature foliage under side: Near RHS Green 138B.
*Venation.*—Type: Pinnate Venation color upper side: Near RHS Green 137A. Venation color under side: Near RHS Green 138B.
Petiole: Basal leaves only
*Length.*—Approximately 2 cm.
*Diameter.*—Approximately 0.4 cm
*Texture.*—Hirsute.

FLOWER

Bloom period: Naturally blooming continuously from Summer to mid-Fall.
Bud:
*Bud shape.*—Flattened globular.
*Bud length.*—Approximately 1.3 cm.
*Bud diameter.*—Approximately 2.4 cm.
*Bud color.*—Near Green 143C. Yellow center near Yellow-Green 144C.
Inflorescence:
*Form.*—Singly occurring composite flowers. Mainly terminal, infrequently axial.
Flower:
*Diameter of entire flower.*—Approximately 8.9 cm.
*Depth of flower.*—Approximately 4.1 cm.
*Disc diameter.*—Approximately 3.2 cm.
*Receptacle shape.*—Rounded.
*Receptacle height.*—Average 0.3 cm.
*Receptacle diameter.*—Average 2.4 cm.
*Quantity of inflorescences per lateral stem.*—1.
*Quantity of open inflorescences and buds per plant.*—Average 11.
*Longevity.*—Average 3 weeks without significant fading or aging. Persistent.
*Rate of opening.*—7 to 14 days from bud to fully opened flower.
Ray florets:
*Arrangement.*—Rotate in a single whorl.
*Aspect/orientation.*—Flat, approximately 75 angle from receptacle.
*Shape.*—Oblanceolate.
*Number of ray florets.*—Avg. 22.
*Length.*—Approximately 2.9 cm.
*Width.*—Approximately 1.5 cm.
*Apex shape.*—Spatulate, very slightly acute tip.
*Base.*—Acute.
*Margin.*—Entire.
*Texture.*—Smooth, slightly ribbed lengthwise.
Color:
*Ray florets*—Upper surface at first opening: Near RHS Yellow-Green 145A. Upper surface at maturity: Near RHS Yellow-Green 150A. Some with bases flushed with Red-Purple 64C. Upper surface at fading: RHS Yellow-Green 154B, all Red-Purple flushing gone. Under surface at first opening: Near RHS Yellow-Green 144C. Under surface at maturity: Near RHS Yellow-Green 150A, some flushing with Red-Purple 64C at very small portion of base. Under surface at fading: RHS Yellow-Green 154B, all Red-Purple flushing gone.
Disc florets:
*Number of disc florets.*—Approximately 250.
*Arrangement.*—Acropetally on disc.
*Length.*—Approximately 1 cm.
*Width.*—Approximately 0.2 cm.
*Shape.*—Cylindric.
*Margin.*—Entire.
*Apex.*—Acute.
*Base.*—Fused, acute.
*Texture.*—Smooth, slightly glossy.
*Receptacle spines.*—Paresent: Number of spines per disc floret: 1. Spine shape: straight. Spine apex: ensiform. Spine texture: smooth. Spine apex color: Near RHS Red 53B. Spine mid-section color: Near RHS Yellow-Orange 21B. Spine base color: Near RHS Yellow-Green 150A.
Color:
*Disc florets.*—At first opening: Near RHS Yellow-Green 151A. At maturity: Near RHS Red-Purple 60A.
Fragrance: Sweet, somewhat lilac-like.
Phyllaries/involucal bracts:
*Arrangement.*—Whorled in 4 rows.
*Number.*—Approximately 70.
*Length.*—Approximately 1 cm.
*Width.*—Approximately 0.4 cm.
*Shape.*—Lanceolate.
*Apex.*—Acute.

*Base.*—Fused.
*Margin.*—Entire.
*Texture.*—Sparsely pubescent.
*Color.*—Inside color near RHS Yellow-Green 147B. Outside color near RHS Yellow-Green 144B.

PEDUNCLE

*Length.*—Average 16.0 cm.
*Width.*—Average 0.6 cm.
*Texture.*—Hirsute.
*Color.*—Near RHS Green 138B.

REPRODUCTIVE ORGANS

Androecium:
*Stamens per disc floret.*—5.
*Filament length.*—Approximately 0.2 cm.
*Filament color.*—Near RHS Yellow-Green 154D.
*Anther shape.*—Narrow cylinder.
*Anther length.*—About 0.1 cm.
*Anther color.*—Near RHS Yellow-Green 144A.
*Pollen amount.*—Scant.
*Pollen color.*—Near RHS Yellow 1A.

Gynoecium:
*Pistil length.*—Approximately 0.3 cm.
*Stigma shape.*—Bi-parted.
*Stigma color.*—Near RHS Yellow-Green 144A.
*Style length.*—About 0.4 cm.
*Style color.*—Near RHS Yellow-Green 144B.
*Ovary color.*—Near RHS Yellow-Green 154D.

OTHER CHARACTERISTICS

Disease resistance: Neither resistance nor susceptibility to diseases or pests has been observed in this variety.
Drought tolerance and temperature tolerance.—Hardy perennial to −15° C. Upper temperature tolerance to at least 35° C. Some drought tolerance, established plants can tolerate infrequent summer waterings.
Fruit/seed production: Fruit and seed production have not been observed in the new cultivar.

What is claimed is:

1. A new and distinct cultivar of *Echinacea* plant named 'Green Queen' as herein illustrated and described.

* * * * *